United States Patent
Drachev et al.

(10) Patent No.: US 7,298,474 B2
(45) Date of Patent: Nov. 20, 2007

(54) PLASMONIC AND/OR MICROCAVITY ENHANCED OPTICAL PROTEIN SENSING

(75) Inventors: Vladimir P. Drachev, West Lafayette, IN (US); Vladimir Shalaev, West Lafeyette, IN (US); Dongmao Zhang, West Lafayette, IN (US); Dor Ben-Amotz, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 390 days.

(21) Appl. No.: 11/102,346

(22) Filed: Apr. 8, 2005

(65) Prior Publication Data

US 2005/0221503 A1    Oct. 6, 2005

(51) Int. Cl.
  *G01J 3/44*    (2006.01)
(52) U.S. Cl. ..................................... 356/301
(58) Field of Classification Search .............. 356/301
  See application file for complete search history.

(56) References Cited

U.S. PATENT DOCUMENTS

| | | | |
|---|---|---|---|
| 5,255,067 A | 10/1993 | Carrabba et al. | |
| 5,504,337 A | 4/1996 | Lakowicz et al. | |
| 5,693,152 A | 12/1997 | Carron | |
| 5,777,776 A | 7/1998 | Hiraga et al. | |
| 5,793,485 A | 8/1998 | Gourley | |
| 6,025,202 A | 2/2000 | Natan | |
| 6,226,082 B1 | 5/2001 | Roe | |
| 6,242,264 B1 | 6/2001 | Natan et al. | |
| 6,256,096 B1 | 7/2001 | Johnson | |
| 6,313,914 B1 | 11/2001 | Roe | |
| 6,514,767 B1 | 2/2003 | Natan | |
| 6,558,956 B1 | 5/2003 | Carron et al. | |
| 6,590,647 B2 | 7/2003 | Stephenson | |
| 6,603,537 B1 | 8/2003 | Dietz et al. | |
| 6,608,716 B1 * | 8/2003 | Armstrong et al. | ......... 359/342 |

(Continued)

OTHER PUBLICATIONS

Alan D. Gift, Jiaying Ma, Kenneth S. Haber, Brian L. McClain and Dor Ben-Amotz, "Near-infrared Raman Imaging Microscope Based on Fiber-bundle Image Compression," *Journal of Raman Spectroscopy*, 30, 757-765 (1999).

(Continued)

*Primary Examiner*—Tarifur Chowdhury
*Assistant Examiner*—Jonathon D Cook
(74) *Attorney, Agent, or Firm*—R. Neil Sudol; Henry D. Coleman; William J. Sapone

(57) ABSTRACT

Instruments for molecular detection at the nano-molar to femto-molar concentration level include a longitudinal capillary column (10) of known wall thickness and diameter. The column (10) contains a medium (24) including a target molecule (30) and a plurality of optically interactive dielectric beads (26) on the order of about $10^{-6}$ meters up to about $10^{-3}$ meters and/or metal nanoparticles (31) on the order of 1-500 nm. A flow inducer (34) causes longitudinal movement of the target molecule within the column (10). A laser (14) introduces energy laterally with respect to the column (10) at a wavelength and in a direction selected to have a resonant mode within the capillary column wall (12) and couple to the medium (24). A detector (40) is positioned to detect Raman scattering occurring along the column (10) due to the presence of the target molecule.

21 Claims, 3 Drawing Sheets

U.S. PATENT DOCUMENTS 6,623,977 B1    9/2003    Farquharson et al.

OTHER PUBLICATIONS

William F. Nirode, Gerald L. Devault and Michael J. Sepaniak, "On-Column Surface-Enhanced Raman Spectroscopy Detection in Capillary Electrophoresis Using Running Buffers Containing Silver Colloidal Solutions," *Analytical Chemistry*, vol. 72, No. 8, 1866-1871 (2000).

Biran L. McClain, Hartmut G. Hedderich, Alan D. Gift, Dongmao Zhang, Karim N. Jallad, Kenneth S. Haber, Jiaying Ma and Dor Ben-Amotz, "Fast Chemical Imaging," *Spectroscopy*, 15(9), 28-37 (2000).

Dongmao Zhang, Jeanette D. Hanna, Yanan Jiang, and Dor Ben-Amotz, "Influence of Laser Illumination Geometry on the Power Distribution Advantage," *Applied Spectroscopy*, vol. 55, No. 1, 61-65 (2001).

* cited by examiner

PLASMONIC AND/OR MICROCAVITY ENHANCED OPTICAL PROTEIN SENSING

BACKGROUND

1. Technical Field

The present invention relates to optical testing and measuring using dispersed light spectroscopy including Raman scattering. The present invention particularly relates to optical testing and measuring based on linear and non-linear optical emissions from an active separation column delivering enhanced molecularly related information pertaining to the contents of the column.

2. General Background

Molecular separation columns have been used for many years to separate and analyze sub-molar, milli-molar, and even micro-molar concentrations of specific organic molecules. Examples of such molecular separation columns include chromatography, electrophoresis, flow cytometry, HPLC, and density gradient separation. As the concentration of a specific organic molecule decreases, the sensing of a reliable indicator for that target molecule becomes increasingly difficult. Much work has been done toward enhancing detection capability so that even smaller molar concentrations can be used as acceptable samples. The ultimate ideal, of course, is to be able to reliably detect the presence of a single target molecule in a given sample. A practical goal is to gather reliable information concerning molecules that are present in nano-molar, pico-molar, and even femto-molar concentrations in a given sample.

A number of techniques are available for gathering information concerning the nature of the molecules in a given sample by virtue of indicative spectral characteristics including UV spectroscopy, IR spectroscopy, Brillouin scattering, Raman scattering, fluorescence spectroscopy, multi-photon fluorescence spectroscopy and mass spectrometry. Surface Enhanced Raman Scattering (SERS), including hyper-Raman scattering, is of particular interest as it tends to give large enhancements of characteristic Raman spectra when the specimen is in the near vicinity of certain materials that can be generally characterized as coinage metals, e.g., gold, silver, copper, nickel, and aluminum in the form of particles or films.

The general techniques of SERS is well established and is discussed to varying degrees in a variety of references ranging from text books to additional patents such as U.S. Pat. No. 5,693,152 to Carron, U.S. Pat. No. 5,255,067 to Carrabba, U.S. Pat. Nos. 5,266,498, 5,376,556, and 5,567,628 to Tarcha, and U.S. Pat. No. 6,608,716 to Armstrong, et al. To the extent necessary, each of these references is hereby incorporated by reference to provide additional understanding as they relate to the Raman and SERS techniques generally.

Optical microcavities are generally dielectric resonant structures that have at least one dimension that is at least on the order of about $10^{-6}$ meters up to about $10^{-2}$ meters. The specific geometry of the microcavity and the boundary conditions on any interface of the dielectric to an adjacent medium impose selective normal modes on the optical microcavity, sometimes referred to as morphology-dependent resonances (MDRs). Such microcavities have been employed at least experimentally to construct light emitting devices. Further, resonant microcavities can emit light in a highly directional manner as a result of their inherent geometry. These resonances, which may have very high quality factors, Q on the order of $10^5$ to $10^{10}$, result from confinement of the radiation within the microcavity by total internal reflection. Light emitted within or scattered in the microcavity may couple to high-Q MDRs lying within its spectral bandwidth, leading to enhancement of both spontaneous and stimulated optical emissions.

Resonant microcavities are known to cause large enhancements of optical emissions. For example, enhanced fluorescence emission from a dye-doped cylindrical or spherical microcavity occurs when either the laser pump or the fluorescence, or both, couple to microcavity MDRs. J. F. Owen, Phys. Rev. Lett. 47, 1075 (1981). Moreover, the increased feedback produced by MDRs is sufficient to obtain laser emission from a dye-doped microdroplet under both a continuous wave (CW) and pulsed laser excitation. H. M. Tzeng, et al., Opt. Lett. 9, 499 (1984); A. Biswas, et al., Opt. Lett. 14, 214 (1988). The existence of high-Q microcavity modes is also responsible for numerous stimulated nonlinear effects including stimulated Raman and Rayleigh-wing scattering and four-wave parametric oscillation under moderate intensity CW excitation. M. B. Lin and A. J. Campillo, Phys. Rev. Lett. 73, 2440 (1994).

Direct on-column SERS detection of $10^{-6}$ M Riboflavin and $10^{-8}$ M Rhodamine 6G has been demonstrated in capillary electrophoresis incorporating buffers containing silver colloidal solutions. The capillaries were $100 \times 10^{-6}$ m inside diameter fused-silica capillaries with an outside diameter of $365 \times 10^{-6}$ m. At the reported molar concentrations for the test compounds, acquisition of satisfactory spectral data could be obtained using a 17 mW laser operating at 515 nm wavelength in about one second. W. F. Nirode, et al., Anal. Chem. 72, 1866 (2000). For lower molar concentrations, commensurately longer data acquisition times are expected. For sub-nanomolar concentrations, the time expected for sufficient data acquisition increases so that so called on-the-fly acquisition is unlikely without other changes to the system.

What is still needed is an instrument for multiplexed protein analysis with enhanced sensitivity and lower recurring chemical costs compared to current proteomic detection and labeling technologies, which is operable on nano-molar and pico-molar, and in some cases even femto-molar concentrations of a given protein in question.

BRIEF SUMMARY OF THE INVENTION

A suitable instrument for molecular detection at the nano-molar to femto-molar concentration level can be constructed to include a longitudinal capillary column having a wall of known thickness and diameter, the column containing a medium to which a molecule sought to be detected can be introduced. A plurality of optically interactive dielectric microparticles having at least one dimension that is at least on the order of about $10^{-6}$ meters up to about $10^{-3}$ meters is situated within the column. Alternatively or additionally, a plurality of nanoparticles having a coinage metal component and an average dimension of about 1-500 nm can be situated within the column. A flow inducer is provided to cause the molecule sought to be detected to flow generally longitudinally through the column from the point of introduction. An optical exciter, typically a laser, is positioned to introduce optical energy laterally with respect to the column at a wavelength selected to have a resonant mode within the capillary column wall. A detector is positioned to detect Raman scattering occurring along the column due to the presence of the molecule sought to be detected together with the microparticles and/or nanoparticles.

The present invention uses the properties of particles within a high-Q microcavity capillary column to achieve an observed optical enhancement that is multiplicative rather than additive of the two processes. The capillary columns of the present invention should generally have a wall thickness on the order of or less than 1 mm. The dielectric microparticles can be in the form of porous glass particles, silica particles, polystyrene or carboxylate microspheres, which can include surface islets of coinage metals that enhance light scattering and SERS interaction with any materials carried by the fluid buffers within the capillary column. The dielectric microparticles can be those developed for use as conventional chromatographic solid supports, or flow cytometry particles, and are available uncoated or derivatized with reactive functional groups such as supports for affinity, ion exchange, and size exclusion chromatography. The kinds of nanoparticles that can be used in the present invention include spherical and non-spherical particles including a coinage metal component with average diameters in the 1 nm to 500 nm range, either in monomeric form or aggregated clusters. The dielectric microparticles can be used, for example, as enzyme reactors, immunosorbents, biosensors, and for solid phase synthesis. Since the nanoparticles and the dielectric microparticles can also produce large optical scattering, they can facilitate the excitation of optical MDR modes within the glass walls of the capillary column. These resonance modes greatly enhance the Raman scattering intensity from proteins and other organic target molecules and compounds in the column. Such optically resonant columns including optically active dielectric microparticles and/or metal component nanoparticles can achieve ultra-low threshold micro-analysis, including spectroscopy of nano-molar, pico-molar, and even femto-molar concentrations of target molecules, and potentially even single molecules.

The Raman signal can be collected at a single point along the column, however, it is preferable that a number of signal collection points be employed. The excitation light and returned sensing signal can be directed using conventional optical elements such as mirrors, lenses, optical filters and diffraction gratings and/or using elements such as optical fibers and holographic materials. The simultaneous detection of multiple wavelengths and/or signals from multiple locations can be facilitated by using a charged coupled device (CCD) detector or other 2-D optical array detectors. Key design criteria associated with the proper functioning of the sensing system include the distribution of optical power so as to avoid optical damage to the sample, thus making the detection non-invasive and repeatable. Protein sensors and sensing systems can incorporate design features based on these principals so as to advantageously enhance the protein chemical and structural information derived from the system. The multiple location signal collection points defined by a 2-D optical array can be distributed at fixed positions along the length of the column to gather information concerning various interactions that take place within the column as a function of longitudinal position. The signal collection points can also be distributed laterally around the column at the same longitudinal position to spatially integrate and thus enhance the signal. The signal collection points can also be movable along the column as a function of time for the purpose of gathering reaction profiles and other similar information. The movement of the signal collection points can be achieved by either a movement of the Raman signal sensors along the column, or by physical movement of the column relative to the sensors, or some combination of the two motions.

The processing of the collected data can involve any number of conventional signal processing techniques that are well known to those skilled in the art. For example, the data can initially be cleaned to remove spectral artifacts such as fluorescence interference and cosmic spikes. In particular, fluorescence background can be reduced with wavelet transformation or derivative methods, and cosmic spikes can be eliminated with Upper Bound Spectra (UBS) or UBS data—matrix (UBS-DM) methods depending on the amount of data gathered during the measurement. Next, it is often desirable to enhance the performance of several commonly used classification algorithms especially when the sample size is limited compared with the number of measurement features. This is achieved by feature selection and/or augmentation. Next the enhanced and/or feature selected portion of the data is subjected to Principal Components Analysis (PCA), Linear Discriminant Analysis (LDA), Quadratic Discriminant Analysis (QDA), Regularized Discriminant Analysis (RDA), Partial Least Squares (PLS) analysis, and combinations thereof with these or other recognized methods to better classify and correlate the observed data with known standards. With the Raman spectra collected from the column at various times and locations, Multivariate Curve Resolution (MCR) methods can be implemented to obtain the pure component spectra and thus derive a chromatogram for individual component under consideration. Then classification methods are applied to the pure component spectra to identify the protein or other organic molecule under investigation.

The present invention can be used to gather information from a wide variety of technologies for proteomic and other sensing applications, either as part of a stand-alone sensor or integrated into a larger protein sensing system, such as one containing chromatographic, electrophoretic or mass spectrometeric components. For example, the present invention can be used to gather data pertaining to the sensitivity to peptide and protein phosphorylation, glycan branching in glycoproteins, peptide and protein conformational changes, and protein binding induced chemical and/or structural changes.

One feature of the present invention is the utilization of a capillary column having a wall dimensioned to permit resonant modes of the introduced optical energy to exist within the column wall and to couple resonant modes with a medium inside the column. This feature has the advantage of significantly enhancing the optical coupling between the introduced optical energy and the various materials present within the column, including at least the target protein or other organic molecule as well as the optically interactive dielectric microparticles that are within the column. The plurality of dielectric microparticles facilitates in turn a coupling of the resonant modes with the target medium.

Another feature of the present invention is that the flow of the target protein or other organic molecule through the length of the column can be achieved by any means capable of generating a migration gradient without affecting the ability to retrieve satisfactory Raman data. This feature allows for the adaptability of the structures of the present invention for Raman data gathering to a broad range of chromatographic, electrophoretic, and other proteomic processes and equipment.

Various other features and advantages of the present invention will be set forth in part in the detailed description to follow, taken in conjunction with the accompanying drawings, and in part will become apparent to those skilled in the art upon examination of the following, or may be learned by a practice of the invention.

DESCRIPTION OF THE PREFERRED EMBODIMENTS

Figure 1:
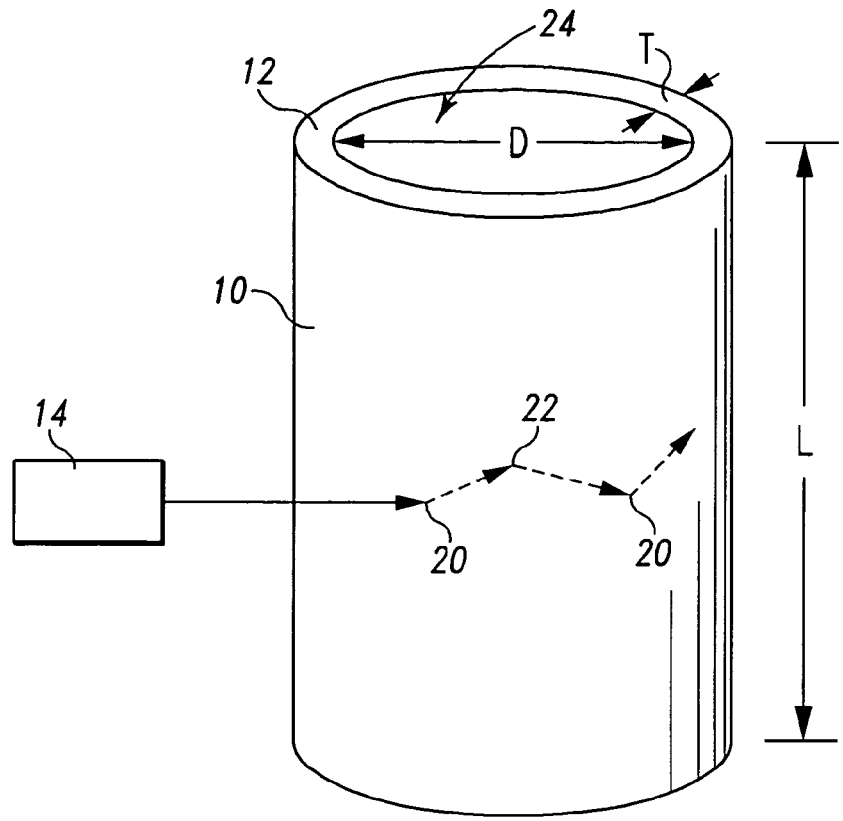
FIG. 1 is a schematic diagram of side view of apparatus of the present invention.
Figure 2:
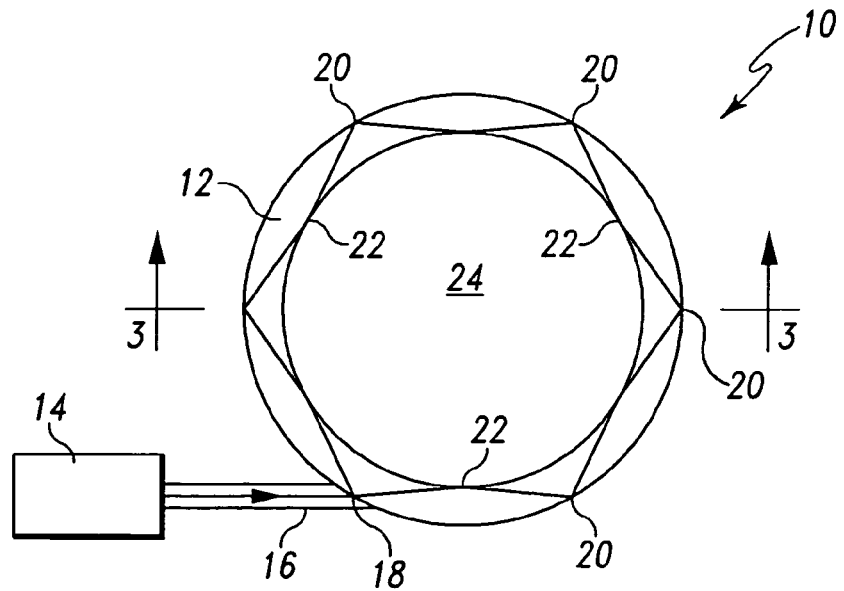
FIG. 2 is a schematic plan view of the apparatus shown in FIG. 1.

FIGS. 1 and 2 show a capillary column 10 of longitudinal dimension L having a cylindrical wall 12 of thickness T and an inside diameter D. FIGS. 1 and 2 are not intended to be scale drawings. The longitudinal dimension L of a capillary column 10 useful in the present invention may be specified by related ancillary equipment such as holders and supports that are not illustrated. A typical longitudinal dimension L could range from about 5 cm or even less to about 50 cm or even more. The inside diameter D of the column 10 should be large enough to contain a sufficient volume of fluid and other materials to permit a normal operation of the column in the usual mode for the particular type of instrumentation involved, e.g., chromatography, electrophoresis, flow cytometry, HPLC, etc. A typical inside diameter D of the column 10 is less than about 3000 μm and preferably less than about 100 μm. The thickness T of the wall 12 should desirably be that which will promote the propagation of incident light to excite the resonant modes around the capillary column 10. One of the possible resonant modes is illustrated schematically in FIG. 2. The thickness T of wall 12 must be sufficient to provide the necessary strength to resist breaking under normal use conditions. A typical wall thickness T for column is generally less than about 200 μm. To increase the coupling of the incident light to the wall cavity modes, a "deformed" cylindrical capillary having an ellipsoidal rather than cylindrical cross-section is advantageous.

An optical exciter 14, typically in the form of a laser, is position to introduce optical energy of known wavelength laterally into the wall 12. The wall 12 has a known index of refraction defining an outside critical angle $\theta_O$ for total internal reflection of light at the outside surface of the wall 12 at the interface with the surrounding air. The optical exciter can include an optical fiber or other coupler 16 of known refractive index that includes an end portion 18 abutting the wall 12 so that optical energy is transferred directly from the optical fiber 16 to the wall 12 at an angle below the outside critical angle $\theta_O$. The optical energy that is transferred into the wall 12 of the column 10 will be reflected at each subsequent outside wall intercept point 20 by total internal reflection toward a next inside wall intercept 22. On the inside surface of the wall 12, the inside critical angle $\theta_I$ can be controlled by controlling the optical density of the medium 24 within the column 10. By suitably selecting the optical density of the medium with the column 10, and by varying the introduction angle of the optical fiber 16 in relation to the outer surface of the wall 12, the optical energy reflected from each of the outside wall intercept points 20 can approach the inside wall intercept points 22 at an angle, near the inside critical angle $\theta_I$, suitable to transfer some, but not all, of the optical energy into the medium 24 within the column at each inside wall intercept point 22, thereby distributing the optical energy around the periphery of the medium 24, with the wall 12 of the column 10 operating in a resonant mode. It will be understood that the particular resonance excited can be a function of the column wall geometry, introduction angle, relative refraction indices, and wavelength.

Figure 3:
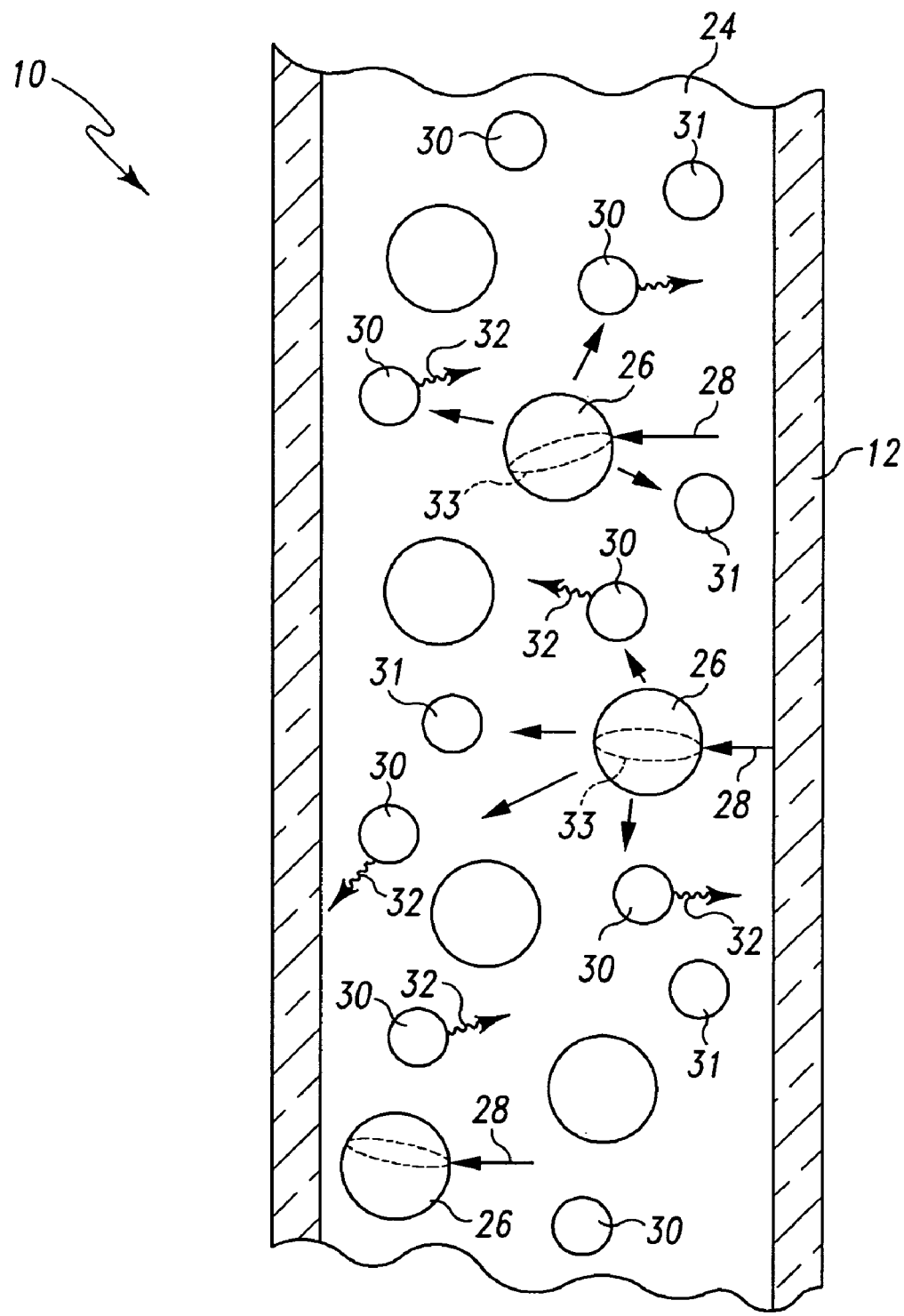
FIG. 3 is a schematic sectional view of the apparatus shown in FIG. 2 taken along line 3-3.

FIG. 3 shows schematically the interior of the column 10 and the interactions that take place in accordance with the present invention. The column 10 includes the medium 24 having a plurality of optically interactive dielectric beads or microparticles 26. The dielectric microparticles 26 have at least one dimension that is at least on the order of about $10^{-6}$ m and have a refractive index that is greater than the surrounding medium 24. The input optical field transferred into the medium 24, from the wall 12 of the column 10 can excite electromagnetic modes in the microparticles 26 as illustrated in schematic FIG. 3 by arrows 28. The microparticles 26 can operate as MDRs to enhance the interaction of the optical energy with the surrounding medium and any constituent molecules 30 including proteins that are in the medium or bound to the microparticles 26. Of course, the input energy from the wall 12 can directly reach the target molecules 30, but when the molar concentration of the target molecules 30 is low, the corresponding interaction cross-section is also low. The interaction particularly desired in the context of the present invention is Raman scattering, but other optical effects can use the desirable attributes of the present invention. The reactive emissions such as Raman spectra from the target molecules 30 are illustrated by arrows 32. The combination of the optically interactive dielectric micropartidles 26 with the resonance behavior of the wall 12 of the column 10 containing the microparticles 26 leads to a dramatic increase in Raman spectral emissions from a sample of given molar concentration. Consequently the detection of the Raman emissions by any means is more easily accomplished. SERS active particles 31 can also be included in the medium 24 to further enhance the Raman emissions. Also, the dielectric microparticles 26 can be coated with thin metal films to facilitate SERS. If the dielectric microparticles 26 are larger than the excitation wavelength, they can support their own optical modes and can increase the coupling to the capillary wall optical modes. If the dielectric microparticles 26 are smaller than the excitation wavelength, they cannot support their own optical modes, but still can increase the coupling to the capillary wall optical modes. Thus, the presence of the dielectric microparticles 26 increases sensitivity of the optical probing regardless of size.

The microcavity structures 12 and 26 enhance the interaction of light with amino-acid, peptide or protein molecules contained within or immediately surrounding such structures. These resonances, which may have extremely high quality factors ($Q=10^4$ to $10^{10}$), result from confinement of the radiation usually by total internal reflection. For example the columns 10 can contain further microcapillary tubes that trap light inside the walls of the microcapillary in such a way as to increase the interaction between the light and the molecules that are in the core of the microcapillary, or adsorbed on the inner, or outer, surface of the microcapillary. The trapping of light can enhance Raman scattering or fluorescence from the molecules and can also beneficially confine and/or direct the scattered or emitted light to enhance the sensitivity and/or resolution with which the light can be detected. Scattering along with absorption can decrease the Q-factor. However, there is also an important positive role of the scattering. When a highly scattering medium 24 is placed in the column 10, the scattering points 31 form secondary sources of radiation in the vicinity of the inner surface of the column 10, which can result in a more efficient coupling to the cavity modes of the column, as described above. Since the scattering points 31 that are smaller than the excitation wavelength can still increase the coupling to the capillary wall modes, such scattering points 31 can also be similarly dimensioned metal particles or aggregates thereof, which provide particularly strong scattering and thus efficient coupling to the capillary modes. In addition to the MDR microparticles 26 and other inorganic particles, enhanced Raman scattering can also occur from proteins such as the target molecules 30 dissolved in a fluid within the capillary and/or adsorbed on the inner surface of the capillary or on the surface of the microparticles. Thus any MDR associated with the capillary 10 and/or the microparticles 26 in the capillary 10 can be advantageous in enhancing the Raman scattering from proteins. A microcavity with MDR supporting fillings can serve as an isolated sensor or a part of a detector for chromatography. Thus when the column 10, or selected region of the column 10, is irradiated with a Raman excitation laser 14 of appropriate wavelength, the protein Raman scattering emanating from the chromatographic peak can be collected and the resulting Raman spectrum stored and processed for the purpose of extracting chemical data about the protein or proteins present in the chromatographic peak. Further benefit can be obtained by coating the microparticles 26 with material which has a differential affinity for proteins with different amino-acid sequences, or proteins with the same amino acid sequence but different post-translational modifications or proteins in different structural conformations or states of aggregation with other proteins or with other chemical species. In particular, such coatings may advantageously serve to preferentially adsorb or adhere to different types of proteins to separate them in time/distance as well as to enhance their Raman scattering by increasing their local concentration without enhancing their overall presence.

The optical detection of protein signals is performed in such a way as to minimize optical losses and interfering signals and maximize signal quality in terms of sensitivity, reproducibility and quantifiability. The optical system can detect a signal from a single location or from multiple locations. The excitation light and returned sensing signal can be directed using conventional optical elements such as mirrors, lenses, optical filters and diffraction gratings and/or using elements such as optical fibers and holographic materials. The simultaneous detection of multiple wavelengths and/or signals from multiple locations can be facilitated by using a charged coupled device (CCD) detector or other two dimensional optical array detectors. Key design criteria associated with the proper functioning of the sensing system include the distribution of optical power in such as way as to avoid optical damage to the sample, thus making the detection non-invasive and repeatable. Protein sensors and sensing systems can incorporate design features based on the above principals in such a way as to advantageously enhance the protein chemical and structural information derived from the a system of the present invention.

Figure 4:
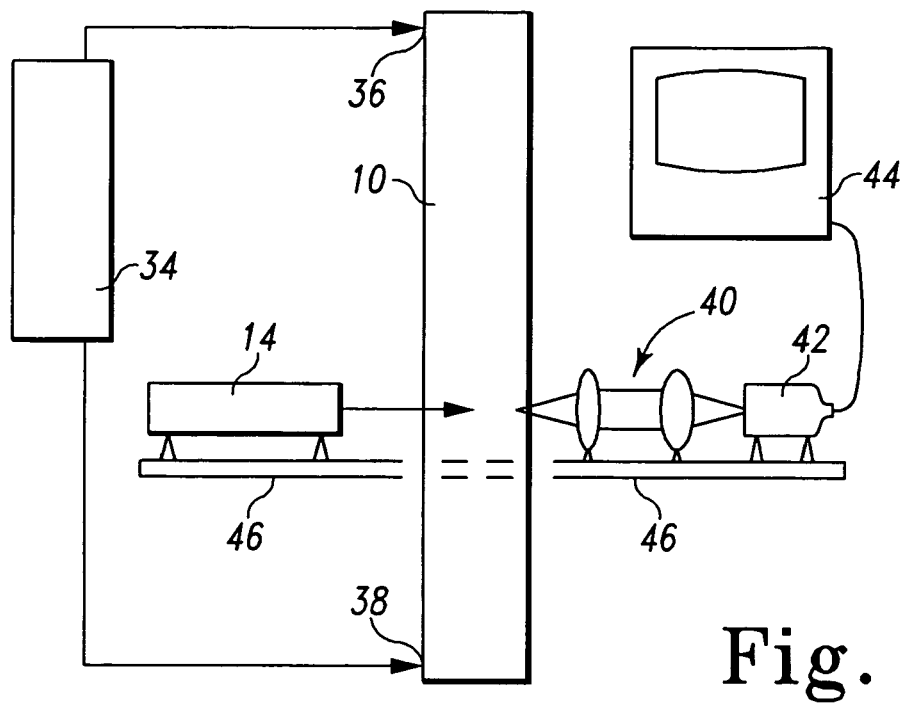
FIG. 4 is a schematic diagram of additional apparatus of the present invention.

One particularly desirable means for detecting the Raman emissions is schematically illustrated in FIG. 4 in which the column 10 and optical exciter 14 are positioned much as in FIG. 1. A suitable flow inducer 34 is coupled to the ends 36 and 38 of the column 10 to cause the target molecules 30 to flow generally longitudinally through the column. The nature of the flow inducer 34 is determined by what other effects are to be coupled with Raman detection, e.g., chromatography, electrophoresis, flow cytometry, HPLC, etc. An optical system 40 is focused on the column to collect any Raman spectral emissions. The optical system 40 directs the collected Raman spectral emissions to a detector 42, which is coupled to a computer 44 programmed to process the information output from the detector. The optical exciter 14, optical system 40 and detector 42 can be mounted on the same platform 46, which can include baffles, filters, and other optical elements well known in the industry for collecting Raman spectral emissions and isolating them from other background radiation. The detector 42 can be a conventional two dimensional planar CCD array. The processing by computer 44 of the output of such arrays 42 is well known and can include such techniques as PCA, LDA, QDA, RDA, PLS, MCR, and combinations thereof with these or other recognized methods. The platform 46 is preferably movable with respect to the column 10. The platform 46 can be a two- or three-dimensionally movable stage on a micro-manipulator capable of moving and positioning the elements mounted thereon in relation to the column 10. The column 10 can also be movable in relation to the platform 46.

Figure 5:
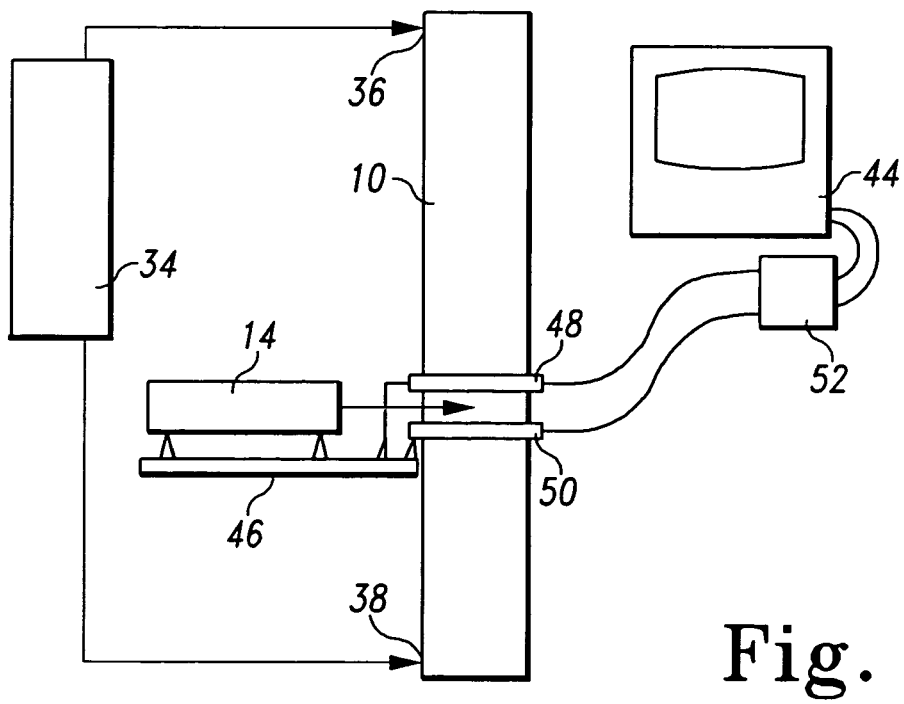
FIG. 5 is a schematic diagram of alternative additional apparatus of the present invention.

Another desirable means for detecting the Raman emissions is schematically illustrated in FIG. 5 in which the column 10 and optical exciter 14 are positioned much as in FIGS. 1 and 4. A suitable flow inducer 34 is coupled to the ends 36 and 38 of the column 10 similar to FIG. 4. A pair of rings 48 and 50 surrounds the column 10, each ring including an inwardly directed array of optical fibers or a similar array of diode detectors for collecting emissions from the column in the vicinity of the input of optical exciter 14. The output of the ring collectors can be processed through a spectrometer 52 or other suitable processing equipment, which is then coupled to computer 44 for processing as previously described in connection with FIG. 4. The rings 48 and 50 are preferable positioned on platform 46. At least one of the pair of rings can be adjustably positioned relative to the platform 46 and the optical exciter 14. The column 10 is preferably movable with respect to the platform 46. As in FIG. 4, the platform 46 can be a two- or three-dimensionally movable stage on a micro-manipulator capable of moving and positioning the elements mounted thereon in relation to the column 10.

The molecular sensors shown in FIGS. 4-5 are based on the measurement of Raman light scattering spectra, which contain molecular vibrational fingerprints with high chemical and structural information content. One advantage of Raman spectroscopy for proteomic sensing applications is that this spectroscopy is capable of measuring parameters such as protein phosphorylation, glycoprotein branching, conformation, and drug binding, which would be difficult or impossible to detect using only chromatographic, electrophoretic or mass spectroscopic proteomic sensing methods. Although Raman spectra are often too weak to allow the detection of proteins at physiological concentrations, the present invention provides optical and material enhancement strategies used to increase the intensity of Raman spectra sufficiently to detect physiological proteins. These strategies, in particular, make use of both column optical containment and optically interactive dielectric particle enhancement of Raman and surface-enhanced Raman scattering spectra. In the latter case metal nanoparticles 31 and/or their aggregates and/or metal thin film coatings 33 on the microparticles 26 can be used. Furthermore, optical multiplexed detection apparatus and methods are employed that facilitate high throughput analysis of surface adsorbed proteins and combinatorial arrays. The present invention combines these enhancement and detection technologies to produce both stand-alone and integrated sensing methodologies which complement and augment the proteomic information content that can be obtained using chromatographic, electrophoretic, mass spectroscopic, and other protein analysis technologies.

Protein sensors based on the present invention can make use of hyper-spectral imaging strategies for multiplexed micro-chemical analysis. This technology, when arranged in structures similar to FIG. 5, allows the multiplexed detection of Raman spectra collected from an array of points within a sample. The technique allows for high throughput detection of proteins when arranged in combinatorial arrays and when distributed on Raman enhancing nano-structured substrates. Such substrates can be composed of nano-structured coinage metals in the form of particles 31 that greatly enhance protein detection sensitivity. These substrates can be formed on the microparticles 26 made of glass, silica or other optically refractive materials, discussed previously, structured so as to produce MDR microcavity enhancement of Raman spectra.

The present invention combines spectral imaging with the SERS/MDR enhancement strategies. The combination can be used to produce powerful new protein sensors as well as hybrid chromatographic and electrophoretic protein sensing technologies and instruments. The advantage of this technology relative to current commercial proteomic detection methods includes greater sensitivity and the ability to determine chemical modifications, including phosphorylation, and structural changes, such as folding, drug binding and complex formation, which cannot be readily detected using existing commercial instrumentation. Furthermore, this technology can be used to produce SERS/MDR/chromatographic instrumentation which combines the selectivity of liquid chromatography with composite pore glass particles inside a resonant wall chromatographic column. The pore glass particles used can be the same as those developed for use as conventional chromatographic solid supports. The pore glass particles are available uncoated or derivatized with reactive functional groups as supports for affinity, ion exchange, and size exclusion chromatography. The pore glass particles can be used, for example, as enzyme reactors, immunosorbents, biosensors, and for solid phase synthesis. Since such glass particles also produce large optical scattering, they facilitate the excitation of optical MDR modes within the chromatographic capillary column and in the glass capillary walls. The resonance modes greatly enhance the Raman scattering intensity from proteins in the column. The present invention combines selectively seeded chromatographic substrate microparticles in optical microcavity capillaries with high throughput detection using the entire column, as shown in FIGS. 4 and 5, rather than merely the end of the column, which is typical of the prior art.

The foregoing detailed description should be regarded as illustrative rather than limiting, and the following claims, including all equivalents, are intended to define the spirit and scope of this invention.

The invention claimed is:

1. A molecular sensor comprising:
   a longitudinal capillary column having a wall of known thickness and diameter, the column containing a medium including a target molecule sought to be detected,
   a plurality of optically interactive particles having at least one dimension that is at least on the order of about $10^{-8}$ meters situated within the column,
   a flow inducer causing the target molecule to flow generally longitudinally through the column,
   an optical exciter positioned to introduce optical energy of known wavelength laterally with respect to the column so as to have a resonant mode within the capillary column wall optically coupled with the medium, and
   a detector positioned to detect Raman scattering occurring in the column due to the presence of the target molecule.

2. The molecular sensor of claim 1 wherein the optically interactive particles comprise dielectric microparticles having at least one dimension that is at least on the order of about $10^{-6}$ meters.

3. The molecular sensor of claim 1 or 2 wherein the longitudinal capillary column comprises a fused silica capillary having a wall thickness of less than about $1000 \times 10^{-6}$ m.

4. The molecular sensor of claim 3 wherein the longitudinal capillary column has a wall thickness of less than about $10 \times 10^{-6}$ m and an inside diameter of less than about $1000 \times 10^{-6}$ m.

5. The molecular sensor of claim 3 wherein the capillary wall is non-cylindrical in cross-section.

6. The molecular sensor of claim 5 wherein the capillary wall is ellipsoidal in cross-section.

7. The molecular sensor of claim 2 wherein the optically interactive particles comprise particles at least partially coated with a coinage metal.

8. The molecular sensor of claim 7 wherein the coinage metal coating thickness is less than about 100 nm.

9. The molecular sensor of claim 2 wherein the optically interactive particles comprise a surface at least partially derivatized with a reactive functional group for interaction with a constituent of the medium.

10. The molecular sensor of claim 1 wherein the optically interactive particles comprise metal nanoparticles having an average size between about 1 and 500 nm, and their aggregates.

11. The molecular sensor of claim 1 wherein the flow inducer comprises a motion inducing gradient applied to the material within the column to cause longitudinal motion of the target molecule.

12. The molecular sensor of claim 1 wherein the optical exciter comprises a laser situated to direct an output beam laterally to intercept a point on the longitudinal capillary outer surface at an angle selected to induce a resonant mode of the output beam energy within the capillary wall.

13. The molecular sensor of claim 1 wherein the detector comprises a two dimensional array of diode sensors and light directing elements for directing spectra from selected points on the longitudinal outer surface to the two dimensional array.

14. The molecular sensor of claim 13 wherein the light directing elements comprise a plurality of lenses focusing a selected portion of the longitudinal capillary outer surface onto the two dimensional array.

15. The molecular sensor of claim 13 wherein the light directing elements comprise a plurality of light pipes having a first end immediately adjacent to the longitudinal capillary outer surface and a second end immediately adjacent to the two dimensional array.

16. A method of sensing a target biomolecule, the method comprising:
   providing a plasmonic substrate in the form of a bead having a minimum linear dimension in at least one direction of about $10^{-8}$ meters, the bead comprising a metal surface;

providing a sample material proximate the surface of the plasmonic substrate by confining the sample material and plasmonic substrate within a column of known wall thickness;

irradiating the column and material therein using light comprising a wavelength such that a resonance mode optically coupled with the sample material is generated within the capillary column wall and Raman scattering occurs within the column;

collecting Raman scattered light from the sample material within the column;

detecting the collected Raman scattered light from the sample material; and determining at least one characteristic of the target molecule within the sample material based on the detected Raman scattered light.

17. The method of claim 16 further comprising the step of applying a motion inducing gradient to the material within the column to cause longitudinal motion of the target molecule within the column.

18. The method of claim 16 wherein the collecting step further comprises, positioning a plurality of sensors adjacent to the column, and sequentially processing an output of the sensors.

19. The method of claim 18 further comprising the step of providing relative movement of the plurality of sensors with respect to the capillary column, and correlating the collecting step with the relative movement.

20. The method of claim 19 wherein the column is moved relative to the plurality of sensors which are maintained in a fixed position.

21. The method of claim 16 further comprising the step of derivatizing at least some of the bead surfaces with a reactive functional group for interaction with a constituent of the sample material.

* * * * *